United States Patent [19]

Mir et al.

[11] 4,241,087
[45] Dec. 23, 1980

[54] DYSMENORRHEA TREATMENT

[75] Inventors: Ghulam N. Mir, Buckingham; Jacqueline B. Krebs, Huntingdon Valley; William L. Studt, Harleysville, all of Pa.

[73] Assignee: William H. Rorer, Inc., Fort Washington, Pa.

[21] Appl. No.: 26,281

[22] Filed: Apr. 2, 1979

[51] Int. Cl.³ .................. A61K 31/165; A61K 31/16; A61K 31/33; A61K 31/155
[52] U.S. Cl. .................. 424/324; 424/244; 424/248.4; 424/250; 424/256; 424/269; 424/270; 424/272; 424/274; 424/304; 424/309; 424/311; 424/319; 424/321; 424/322; 424/326
[58] Field of Search .............. 424/304, 322, 324, 326, 424/244, 248.4, 250, 256, 269, 270, 272, 274, 309, 311, 319, 321; 544/63

[56] References Cited

U.S. PATENT DOCUMENTS 4,060,635  11/1977  Diamond et al. .............. 424/304 X
4,115,647   9/1978  Douglas et al. .............. 544/63

OTHER PUBLICATIONS

Arzneimftel Forschung, 28(11), 1978, pp. 1433-1480.
Prostaglandins, vol. 11, 1976, pp. 893-903.

Primary Examiner—Anna P. Fagelson
Attorney, Agent, or Firm—Ernest G. Szoke

[57] ABSTRACT

Amidinoureas of the formula:

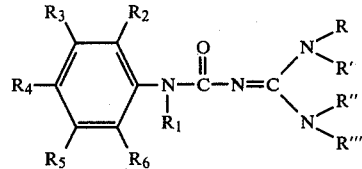

when administered to females who suffer dysmenorrhea relieve discomfort and pain and prevent damage caused by abnormal uterine muscle spasms incident to dysmenorrhea.

18 Claims, No Drawings

DYSMENORRHEA TREATMENT

BACKGROUND OF THE INVENTION

Dysmenorrhea or menstrual pain is the most common of all gynecological disorders in thirty to forty percent of postpubescent females. Though the etiology of primary dysmenorrhea has not been established, it is known that dysmenorrheic subjects show evidence of a higher prostaglandin activity in their menstrual fluid. It is also known that prostaglandins have a powerful uterine stimulating activity, and many researchers believe that dysmenorrhea and menstrual pain from abnormal uterine muscle contraction are associated with the higher prostaglandin levels in dysmenorrhea subjects. Continued or prolonged dysmenorrhea may result in more severe disorders such as endometriosis.

In general, non-sterioldal anti-inflammatory agents prevent the synthesis of prostaglandins and thus find some use in relieving pain in primary dysmenorrhea, but these drugs also prolong the bleeding time, due to their inhibition of platelet aggregation time. Other classes of drugs, e.g. anticholinergics and tranquilizers have found little use in this disorder.

Amidinoureas are known to have a variety of pharmacological effects and in particular, certain substitued amidinoureas are disclosed in U.S. Pat. No. 4,115,647 as having the property of producing a considerable spasmolytic action on the gastrointestinal musculature. Other amidinoureas have been described in U.S. Pat. No. 4,060,635 as having anti-diarrheal properties which implies an antimotility effect related to spasmolytic action on the gastrointestinal musculature.

It has now unexpectedly been found that certain amidinoureas possess valuable pharmacological properties and these compounds exhibit an unexpected capability of inhibiting oxytocin and prostaglandin-induced contractions in In Vitro preparations. Abnormal uterine muscle contractions during the menstrual cycle in dysmenorrhea subjects are due to elevated levels of prostaglandin, therefore, certain amidinoureas will be efficacious in the treatment of dysmenorrhea. Unlike known anti-diarrheal agents that are generally available, such as diphenoxylate hydrochloride and loperamide, which are not effective in the treatment of dysmenorrhea, the amidinoureas appear to exert their activity on uterine muscle by acting beyond the prostaglandin receptor sites in a more fundamental way within the muscle membrane or contractile fiber which makes them particularly useful in the treatment of muscle spasms associated with primary dysmenorrhea. Depending on the particular situation, these amidinoureas may also inhibit prostaglandin-induced diarrhea, which at times accompanies dysmenorrhea.

It has also been found that these amidinoureas, which are easily absorbed from the stomach, have a low order of toxicity so that orally administering amidinoureas to females provides a simple and effective method for preventing and treating dysmenorrhea. Further, in accordance with this invention, a therapeutic program of treatment with an amidinourea can be the basis for relief from the pain of primary dysmenorrhea or, if started early in females having a tendency towards dysmenorrhea, amidinoureas administered continually in effective amounts can prevent the development of endometriosis and other severe conditions resulting from repeated dysmenorrhea.

DESCRIPTION AND PREFERRED EMBODIMENTS

The present invention relates to a new method for inhibiting uterine muscle spasms associated with dysmenorrhea by the administration of amidinoureas. More particularly, the present invention describes a method for preventing and treating dysmenorrhea in humans or mammals by the oral or parenteral administration of an effective amount of an amidinourea of Formula I below:

$$\underset{R_5}{\underset{R_4}{\underset{|}{\bigcirc}}}\overset{R_3}{\underset{R_6}{\overset{R_2}{\bigcirc}}} - \underset{R_1}{N} - \overset{O}{\overset{\|}{C}} - N = C \overset{N \overset{R}{\underset{R'}{\diagdown}}}{\underset{N \overset{R''}{\underset{R'''}{\diagdown}}}{\diagup}} \quad I$$

where:

$R_2$, $R_3$, $R_4$, $R_5$ and $R_6$ may be the same or different and are:
  hydrogen,
  halo,
  lower alkyl,
  halo lower alkyl,
  nitro,
  lower alkoxy,
  hydroxy,
  aryllower alkoxy,
  acyloxy,
  cyano,
  halo lower alkoxy or,
  lower alkyl sulfonyl;
R and R' are hydrogen or lower alkyl;
R" and R'" are
  hydrogen,
  lower alkyl,
  lower alkoxy,
  lower alkenyl,
  cyclo alkenyl,
  cyclo alkyl lower alkyl,
  cyclo alkyl,
  aralkyl,
  lower alkynyl,
  halo alkyl,
  hydroxy alkyl,
  alkoxyalkyl,
  cyano alkyl,
  amino alkyl,
  mono- and di- lower alkyl amino alkyl,
  carbamoyl alkyl,
  mono- and di- carbamoyl alkyl,
  carboxy alkyl,
  alkoxy carbonyl alkyl,
  aralkoxy carbonyl alkyl,
  formyl,
  acyl,
  acyl alkyl,
  alkyl sulfonyl or,
  aralkyl sulfonyl;
R" and R'" together may form a 5 to 7 atom ring which may include 0 to 2 hetero atoms of N, O or S; $R_1$ is hydrogen or it may be lower alkyl provided at least one of R, R', R" and R'" is other than hydrogen; and, the nontoxic pharmaceutically acceptable salts thereof.

Compounds of this invention which are preferred include those where:

R$_2$, R$_3$, R$_4$, R$_5$ and R$_6$ are
  hydrogen,
  halo,
  lower alkyl,
  halo lower alkyl,
  nitro,
  hydroxy, or
  lower alkoxy; and,
R' and R$_1$ are hydrogen or lower alkyl; and
R'' and R''' are hydrogen,
  alkyl or
  alkoxy; provided R, R', R'' and R''' are not all hydrogen at the same time.

The more preferred compounds of this invention include those where:

R$_2$ is hydrogen or lower alkyl;
R$_3$ and R$_5$ are
  hydrogen,
  hydroxy or
  lower alkoxy;
R$_4$ is
  hydrogen,
  lower alkyl,
  hydroxy,
  lower alkoxy or
  halo;
R$_6$ is
  hydrogen,
  lower alkyl,
  nitro,
  alkoxy or
  halo;
R and R$_1$ are hydrogen or lower alkyl; and
R' and R'' are hydrogen or alkyl; provided R, R', R'' and R''' are not all hydrogen at the same time.

The most preferred compounds of this invention are those where:

R$_2$ is
  hydrogen,
  methyl,
  ethyl,
  chloro or
  bromo;
R$_3$ is
  hydrogen,
  hydroxy, or
  methoxy;
R$_4$ is
  hydrogen,
  methyl,
  ethyl,
  hydroxy,
  methoxy,
  chloro or
  bromo;
R$_5$ is
  hydrogen,
  hydroxy or methoxy;
R$_6$ is
  hydrogen,
  methyl,
  ethyl,
  nitro,
  methoxy,
  ethoxy,
  chloro,
  bromo or
  fluoro;
R and R$_1$ are
  hydrogen,
  methyl or
  ethyl; and
R' and R'' are
  hydrogen,
  methyl,
  ethyl,
  propyl,
  i-propyl,
  butyl,
  i-butyl,
  sec-butyl,
  t-butyl,
  methoxy,
  ethoxy,
  propoxy,
  butoxy,
  isopropoxy,
  isobutoxy,
  t-butoxy,
  pentyl,
  hexyl or
  heptyl; provided R, R', R'' and R''' are not all hydrogen at the same time.

A special embodiment of this invention comprises compounds which have:
R$_2$-lower alkyl substitution;
R$_2$, R$_6$-dilower alkyl substitution;
R$_2$, R$_6$-lower alkyl, alkoxy substitution,
R$_2$, R$_6$-lower alkyl, halo substitution;
R$_2$, R$^6$-alkyl, nitro substitution;
R$_2$, R$_4$, R$_6$-trilower alkyl substitution, or
R$_2$, R$_4$, R$_6$-lower alkyl, dihalo substitution.

A further special embodiment of this invention comprises compounds
which have:
  R, R', R'' and R''' as hydrogen or lower alkyl substitution provided all are not hydrogen at the same time; or,
  R and R' are hydrogen or lower alkyl and R'' and R''' are an alkyl or alkoxy group from 3 to 7 carbon atoms.

The compounds of Formula I and the method of preparing them is described in U.S. Pat. No. 4,060,635 and in *Arzneimittel Forschung*, 28 (II), 1433–1480 (1978), the disclosures of which are incorporated herein by reference.

As is known, certain compounds of Formula I can exist in enolized or tautomeric forms or may be obtained as hydrates or in different polymorphic forms. Illustrative of tautomeric forms are the compounds of Formula I wherein R is hydrogen, in which case the compounds may exist in the alternative structural forms shown below:

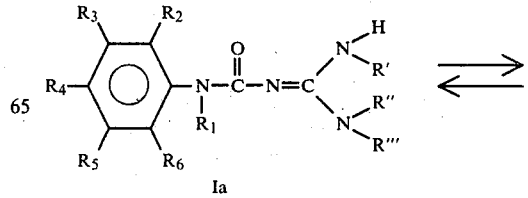

Ia

-continued

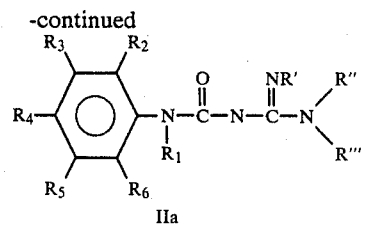

IIa

It is understood that the designations of the amidinoureas suitable for use in the practice of this invention are intended to include the compounds specifically named or shown by structure along with the alternative or transient states where such exist. It is also intended to include the pharmaceutically acceptable salts of the amidinoureas designated by Formula I. Such salts include the non-toxic acid addition salts as well as other salts for example, quarternary ammonium salts.

In accordance with this invention, it has now been found that amidinoureas of Formula I non-specifically inhibit prostaglandin and oxytocin-induced uterine contractions without inhibiting blood platelet aggregation and accordingly, these compounds can be used to reduce abnormal uterine contractions to normal physiological levels without affecting bleeding time in menstruating females. Furthermore, these compounds, when used in a regular therapeutic program for treating patients who suffer dysmenorrhea, can effectively prevent or alleviate secondary dysmenorrhea and the symptons of secondary dysmenorrhea, especially endometriosis. Accordingly, these compounds are useful when administered in therapeutically-effective amounts for the prevention or relief of primary dysmenorrhea and for the prevention or relief of endometriosis. For these purposes, they can be administered orally, parenterally, rectally, or intravaginally. Administration by the oral route is preferred. Orally, these compounds may be administered in tablets, hard or soft capsules, aqueous or oily suspensions, dispersible powders or granules, emulsions, syrups or elixers. The optimum dosage, of course, will depend on the particular compound being used and the type and severity of the condition being treated. In any specific case, the appropriate dosage selected will further depend on factors of the patient which may influence response to the drug; for example, general health, age, weight, etc. of the subject being treated.

Although the optimum quantities for administration of the compounds of Formula I, in accordance with the present invention, will depend on the compound employed and the particular type of disease condition treated, oral dose levels of preferred compounds when administered to human or other mammalian females in dosages of b 0.05 to 50 milligrams per kilogram of body weight per day are particularly useful. The preferred range is 0.1 to 20 mg/kg. Comparative dosages may be used in parenteral or rectal administration.

Compositions intended for oral use may be prepared according to methods known to the art for the manufacture of pharmaceutical compositions. Such compositions may contain one or more agents selected from the group consisting of sweetening agents, flavoring agents, coloring agents, preserving agents, etc. in order to provide a pharmaceutically elegant and platable preparation.

Further, the active amidinourea may be administered alone or in admixture with other agents having the same or different pharmacological properties. The compositions may contain such selected excipients such as inert diluents such as calcium carbonate, lactose, etc; granulating and disintegrating agents such as magnesium stearate, etc.; binding agents such as starch gelatin, etc.; suspending agents such as methylcellulose, vegetable oil, etc.; dispersing agents such as lecithin, etc.; thickening agents such as beeswax, hard paraffin, etc.; emulsifying agents such as naturally-occurring gums, etc.; non-irratating excipients such as cocoa butter, polyethylene glycols, etc.; and the like. Further, in formulating these compounds for every 100 parts by weight of the composition, there may be present between 5 and 95 parts by weight of the active ingredient. The dosage unit form will generally contain between 0.1 mg and about 500 mg of the active ingredient of this invention. The preferred unit dose is between 1 mg and about 50 mg. The compositions may be taken 1 to 8 time daily depending on the dosage unit required.

In a preferred form, the compounds of this invention are prepared for oral administration in either tablet or capsule form depending upon the solubility and capability of the specific amidinourea chosen and the other ingredients. In another preferred form, this invention is practiced by providing an effective amount of an amidinourea of Formula I, generally between about 5 and 10 mg in a single tablet or capsule suitable for oral administration to be administered about twice daily at a dose level of 1 to 2 tablets or capsules.

In general, the dosage regimen in carrying out the methods of this invention is that which insures maximum therapeutic response until improvement is obtained and thereafter, the minimum effective level which gives relief. Generally, the daily dose can be between about 0.1 mg/kg and 70 mg/kg (preferably in the range of 1 to 25 mg/kg/day), bearing in mind, or course, that in selecting the appropriate dosage in any specific case, consideration must be given to the patient's weight, general health, age and other factors which may influence response to the drug.

Various tests in animals have been carried out to show the ability of the compounds of this invention to inhibit uterine muscle spasms. These tests involve the effect of the amidinoureas of Formula I on uterine muscle spasms in the presence of known spasmogens. It has been found that the compounds of this invention when tested in the above situations, show a marked activity.

ISOLATED RAT UTERINE MUSCLE

Female virgin Wistar rats at an average weight of 160 g to 220 g are used for the experiment. Prior to the experiment, the animals are housed five per group and maintained according to standard animal husbandry procedures. The animals are treated with DES (100 mg/kg/body weight) 24 hours prior to the experiment.

The stage of the estrus cycle is determined by vaginal smears on the morning of the experiment. Rats in estrus are killed by a blow on the head and the abdomen is opened. The two horns of the uterus are dissected out and transferred to a dish containing Bathing's solution (composition in g: NaCL, 8.046; KCl, 0.20; $CaCl_2.2H_2O$, 0.132; $MgCl_2.6H_2O$, 0.106; $NaHCO_3$, 1.0; $NaH_2PO_4$, 0.065; Dextrose, 1.0 distilled to 1 liter with distilled water). The two horns are separated and freed from mesentery in Bathing's solution. A thread is attached at each end of each horn and the uterine segment is mounted in a tissue bath (50 ml), maintained at 37° C. by a circulatory bath and aerated with 95% $O_2$ 5% $CO_2$.

One thread is attached to a fixed pin and the other to a transducer. Contractions are recorded isometrically on a Beckman dynograph in conjunction with a Grass force-displacement transducer (FTO3C) of which has been calibrated in g. tension, or isotonically in conjunction with a Harvard smooth muscle transducer (386). The tissue is subjected to a baseline tension of 0.5 g. The preparation is allowed to equilibrate for 30 minutes prior to the experiment.

Various spasmogens (such as: acetylcholine chloride, $PGF_{2a}$, $PGE_2$, oxytocin, $BaCl_2$ or ergonivine maleate) may be used to induce contractions in the isolated uterine strip. See "In Vitro Methodology for Evaluation of Compound Effect on Isolated Guinea Pig Ileum" for description of obtaining dose response curve. Afer the control dose-response curve is obtained, the tissue is allowed to relax for five minutes before the addition of the spasmolytic drug (inhibitory drug). The test drug is in contact with the tissue for two minutes before the dose-response curve is repeated. The inhibitory effect of the test drug is determined as follows:

% Maximum Response =
$$\frac{\text{g tension developed with spasmogen + test drug}}{\text{g tension developed with spasmogen}} \times 100$$

The % maximum response is calculated for each dose of the dose-response curve and the control and drug curves are plotted.

EFFECT OF 1-(2',6'-DIMETHYLPHENYL)-3-METHYL-AMINDINOUREA HYDROCHLORIDE ON Ach, OXYTOCIN AND $PGF_{2a}$-INDUCED CONTRACTIONS IN THE GRAVID RAT UTERUS

The dose-response behavior on the isolated gravid rat uterus of Acetylcholine chloride, Oxytocin and $PGF_{2a}$ was compared in the presence and absence of varying doses of 1-(2',6'-dimethylphenyl)-3-methylamidinourea hydrochloride using the non-cumulative dose response method. The stimulatory effect of these spasmogens on the isolated gravid rat uterus prepartion was recorded using the isometric method to record the contractions induced (See Methodology). The inhibitor effect of 1-(2',6'-dimethylphenyl)-3-methylamidinourea hydrochloride on the spasmogen induced contractions in the In Vitro gravid rat uterus preparation was demonstrated by increasing doses of 1-(2',6'-dimethylphenyl)-3-methylamidinourea hydrochloride. The inhibition by 1-(2',6'-dimethylphenyl)-3-methylamidinourea hydrochloride was dose dependent with all three spasmogens (See Tables).

TABLE I

% Inhibition of Ach Induced Contractions by 1-(2',6'-dimethylphenyl)-3-methyl-amidinourea hydrochloride

| Ach µg/ml | 40 µg/ml* | 80 µg/ml* | 160 µg/ml* |
|---|---|---|---|
| 20 | 100.0 | 100.0 | 100.0 |
| 40 | 83.0 | 100.0 | 100.0 |
| 80 | 79.7 | 100.0 | 100.0 |
| 160 | 46.8 | 95.8 | 100.0 |
| 320 | 2.8 | 26.8 | 93.3 |
| 640 | <2.8 | <26.8 | 93.6 |
| 1,280 | | | 84.6 |
| 2,560 | | | 67.4 |
| 5,120 | | | 61.2 |

TABLE I-continued

% Inhibition of Ach Induced Contractions by 1-(2',6'-dimethylphenyl)-3-methyl-amidinourea hydrochloride

| Ach µg/ml | 40 µg/ml* | 80 µg/ml* | 160 µg/ml* |
|---|---|---|---|
| 10,240 | | | 62.7 |

*Concentration of 1-(2'6'-dimethylphenyl)-3-methylamidinourea hydrochloride

TABLE II

% Inhibition of Oxytocin Induced Contractions by 1-(2',6'-dimethylphenyl)-3-methylamidinourea hydrochloride

| Oxytocin U/ml | 40 µg/ml* | 80 µg/ml* | 160 µg/ml* |
|---|---|---|---|
| $1 \times 10^{-5}$ | 100 | 100.0 | 100.0 |
| $3 \times 10^{-5}$ | 22.1 | 48.7 | 100.0 |
| $1 \times 10^{-4}$ | <22.1 | 14.4 | 100.0 |
| $3 \times 10^{-4}$ | | <14.4 | 63.2 |
| $1 \times 10^{-3}$ | | | 47.6 |
| $3 \times 10^{-3}$ | | | 32.5 |

*Concentration of 1-(2'6'-dimethylphenyl)-3-methylamidinourea hydrochloride

TABLE III

% Inhibition of $PGF_{2\alpha}$ Induced Contractions by 1-(2',6'-dimethylphenyl)-3-methyl-amidinourea hydrochloride

| $PGF_{2\alpha M}$ | 40 µg/ml* | 80 µg/ml* | 160 µg/ml* |
|---|---|---|---|
| $1 \times 10^{-8}$ | 99.0 | 98.2 | 100.0 |
| $3 \times 10^{-8}$ | 95.1 | 91.3 | 100.0 |
| $1 \times 10^{-7}$ | 39.5 | 64.0 | 98.5 |
| $3 \times 10^{-7}$ | <39.5 | 48.9 | 96.1 |
| $1 \times 10^{-6}$ | | <48.9 | 96.1 |
| $3 \times 10^{-6}$ | | | 86.8 |

*Concentration of 1-(2'6'-dimethylphenyl)-3-methylamidinourea hydrochloride

In view of the results of these tests, the pharmacological data clearly indicates thhat the amidinoureas of Formula I can be considered to be effective in inhibiting uterine muscle spasms associated with dysmenorrhea and are useful in preventing and treating dysmenorrhea or menstrual cramps.

Whereas applicant has set forth herein what is believed to be the mode of action of the amidinoureas when used to treat primary dysmenorrha or secondary dysmenorrha, particularly endometriosis, it is to be understood that applicant does not wish to be bound by any particular theory, and the pharmacological tests and examples given herein are by way of illustration only.

The following examples illustrate the preparation of tablets and capsules which constitute the preferred dosage forms for oral administration of the compounds of Formula I in accordance with the method of this invention:

EXAMPLE 1

A batch of homogenous tablets was prepared, each having the following formula:

| Per Tablet | Ingredients | Per 100 Tablets |
|---|---|---|
| 5 mg | 1-(2',6'-dimethyl phenyl)-3-methyl amidinourea hydrochloride (lidamidine hydrochloride) | 5 gm |
| 100 mg | Microcrystalline, Cellulose | 100 gm |
| 150 mg | Cornstarch | 150 gm |

| Per Tablet | Ingredients | Per 100 Tablets |
|---|---|---|
| 450 mg | Deionized water | 450 gm |
| 10 mg | Hydrogenated Castor Oil | 10 gm |
| 715 mg | | 715 gm |

The following procedure is used to prepare the tablets: 1-(2'6'-dimethylphenyl)-3-methyl amidinourea, cellulose and 100 gm of starch are blended together dry. A paste of the remaining starch is prepared with deionized water in a steamed jacketed pot. The two components are mixed, granulated and passed through a #8 screen then dried in a Fluid Bed Dryer at about 40° C. and again passed through a #14 mesh screen. The composition is then formed into tablets by compressing on a Stokes Rotary Multi-Layer Tablet Press.

EXAMPLE 2

Therapeutic compositions of the invention are prepared by using known techniques for compounding employing either the base of a salt as the active ingredient along with non-toxic excipients chosen in accordance with the particular form and properties desired for the therapeutic composition. Other therapeutic agents such as analgesics, tranquilizers, etc. may be added as desired.

Tablets which can be advantageously used for either remedial or prophylactic treatments for dysmenorrhea ordinarily accompanied by abnormal uterine muscle action, can be provided in a form which provides relief from dysmenorrhea symptoms when taken at a rate of 1 to 2 tablets twice daily containing between about 5 to 10 mg of the active ingredient. An exemplary formulation which can be utilized is, for example, the following:

| 1-(2'6'-dimethylphenyl)-3-methylamidinourea | 5 mg |
|---|---|
| tricalcium phosphate | 200 mg |
| talc | 50 mg |
| magnesium stearate | 10 mg |
| polyvinyl acetate | 40 mg |

In addition, there are added protective excipients such as ethylcellulose, dibutylphthalate, propylene glycol, wax (white and/or carbauba), spermaceti, methylene chloride, and rectified diethyl ether. The ingredients are compressed to minimum size to provide a tablet of about 310 mg.

EXAMPLE 3

A lot of 1,000 tablets each containing 1 g of 1-(2'6'-diethylphenyl)-3-methylamidinourea is prepared from the following types and amounts of ingredients:

| 1-(2'6'-diethylphenyl)-3-methyl amidinourea hydrochloride | 10 g |
|---|---|
| dicalcium phosphate | 1 kg |
| methylcellulose USP | 75 kg |
| talc | 150 g |
| cornstarch | 200 g |
| magnesium stearate | 10 g |

The active ingredient and dicalcium phosphate are mixed thoroughly and granulated with a 7.5% solution of methylcellulose in water and passed through a #8 screen and air-dried. The dried granules are passed through a #12 screen and combined with the talc, starch and magnesium stearate with thorough mixing after which the composition is compressed into tablets.

EXAMPLE 4

A lot of 2-piece hard gelatin capsules, each containing 5 mg of 1-(2'6'-dimethylphenyl)-3-methyl amidinoruea are prepared from the following types and amounts of ingredients (the amounts given are per capsule):

| 1-(2'6'-dimethylphenyl)-3-methyl amidinourea hydrochloride | 5 g |
|---|---|
| dicalcium phosphate | 500 g |
| talc | 150 g |
| magnesium stearate | 5 g |

The ingredients are mixed thoroughly and filled into capsules which are used for oral administration at the rate of about one every four hours. If desired, slow release forms can be provided or delayed release forms depending on choice of capsules and formulating ingredients.

By analogous methods and employing techniques known to the art, there are prepared formulations suitable for administration of an effective amount of any of the amidinoureas of Formula I. In particular, by analogy of the processes described above, single dose preparations suitable for oral administration can be readily prepared from the following illustrative amidinoureas:

1-(2'-methyl, 4'6'-dichlorophenyl)-3-methyl amidinourea 1-(2'-chloro, 6'-methylphenyl)-3-amidinourea hydrochloride 1-(2'-methyl, 6'-bromo)-3-amidinourea 1-(2'-methyl, 6'-methoxy)-3-amidinourea hydrochloride 1-(2'-methyl, 6'-ethyl)-3-amidinourea 1-(2'-methyl, 6'-methoxy)-3-methyl amidinourea 1-(2'6'-dimethylphenyl)-3-amidinourea 1-(2'6'-diethylphenyl)-3-amidinourea 1-(2'6'-diethylphenyl)-3-methyl amidinourea 1-(2'6'-dimethylphenyl)-3-methoxy amidinourea 1-(2'6'-diethylphenyl)-3-methoxy amidinourea.

What is claimed is:

1. A method for treating uterine muscle spasms associated with dysmenorrhea which comprises the oral or parenteral administration of an effective amount therefor of an amidinourea of the general formula:

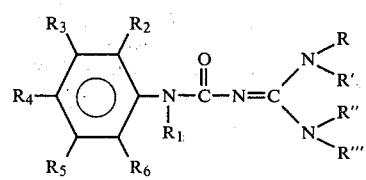

where:

$R_2$, $R_3$, $R_4$, $R_5$ and $R_6$ may be the same or different and are:

hydrogen, halo, lower alkyl, halo lower alkyl, nitro, lower alkoxy hydroxy, aryllower alkoxy, acyloxy, cyano,
halo lower alkoxy or
lower alkyl sulfonyl;
R and R' are hydrogen or lower alkyl;
R" and R'" are
hydrogen,
lower alkyl,
lower alkoxy,
lower alkenyl,
cyclo alkenyl up to 9 carbon atoms,
cyclo alkyl lower alkyl,
lower alkyl,
cyclo alkyl,
aralkyl,
lower alkynyl,
halo alkyl,
hydroxy alkyl,
alkoxy alkyl,
cyano alkyl,
amino alkyl,
mono- and di- lower alkyl amino alkyl
carbamoyl alkyl,
mono- and di-carbamoyl alkyl,
carboxy alkyl,
alkoxy carbonyl alkyl,
aralkoxy carbonyl alkyl,
acyl,
acylalkyl,
alkylsulfonyl or
aralkyl sulfonyl;
R" and R'" together may form a 5 to 7 atom ring which may include 0 to 2 hetero atoms of N, O or S;
R₁ is hydrogen or lower alkyl provided at least one of R, R', R", and R'" is other than hydrogen; and the pharmaceutically-acceptable salts thereof.

2. The method of claim 1 wherein the amidinourea is 1-(2'6'-dimethylphenyl)-3-methylamidinourea.

3. The method of claim 1 wherein the amidinourea is 1-(2'6'-dimethylphenyl)-3-methylamidinourea hydrochloride.

4. A method for the treatment of primary dysmenorrhea which comprises administering to a menstruating female an effective amount therefor of an amidinourea of the formula:

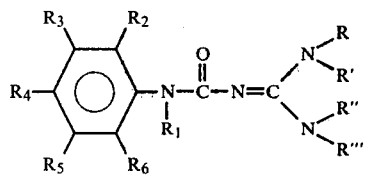

where:
R₂, R₃, R₄, R₅ and R₆ may be the same or different and are:
hydrogen,
halo,
lower alkyl,
halo lower alkyl,
nitro,
lower alkoxy
hydroxy,
aryllower alkoxy,
acyloxy,
cyano,
halo lower alkoxy or
lower alkyl sulfonyl;
R and R' are hydrogen or lower alkyl;
R" and R'" are
hydrogen,
lower alkyl,
lower alkoxy,
lower alkenyl,
cyclo alkenyl up to 9 carbon atoms,
cyclo alkyl lower alkyl,
lower alkyl,
cyclo alkyl,
aralkyl,
lower alkynyl,
halo alkyl,
hydroxy alkyl,
alkoxy alkyl,
cyano alkyl,
amino alkyl,
mono- and di- lower alkyl amino alkyl
carbamoyl alkyl,
mono- and di-carbamoyl alkyl,
carboxy alkyl,
alkoxy carbonyl alkyl,
aralkoxy carbonyl alkyl,
acyl,
acylalkyl,
alkylsulfonyl or
aralkyl sulfonyl;
R" and R'" together may form a 5 to 7 atom ring which may include 0 to 2 hetero atoms of N, O or S;
R₁ is hydrogen or lower alkyl provided at least one of R, R', R", and R'" is other than hydrogen; and the pharmaceutically-acceptable salts thereof.

5. The method of claim 4 wherein the amidinourea is 1-(2'6'-dimethylphenyl)-3-methylamidinourea.

6. The method of claim 4 wherein the amidinourea is 1-(2'6'-dimethylphenyl)-3-methylamidinourea hydrochloride.

7. A method of reducing abnormal uterine muscle action to normal levels which comprises administering an effective amount therefor of a compound of the formula:

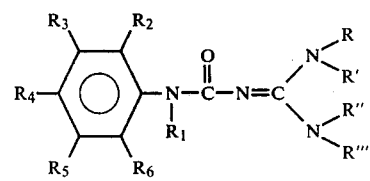

where:
R₂, R₃, R₄, R₅ and R₆ may be the same or different and are:
hydrogen,
halo,
lower alkyl,
halo lower alkyl,
nitro,
lower alkoxy
hydroxy,
aryllower alkoxy,
acyloxy,
cyano,
halo lower alkoxy or
lower alkyl sulfonyl;
R and R' are hydrogen or lower alkyl;

R″ and R‴ are
  hydrogen,
  lower alkyl,
  lower alkoxy,
  lower alkenyl,
  cyclo alkenyl up to 9 carbon atoms,
  cyclo alkyl lower alkyl,
  lower alkyl,
  cyclo alkyl,
  aralkyl,
  lower alkynyl,
  halo alkyl,
  hydroxy alkyl,
  alkoxy alkyl,
  cyano alkyl,
  amino alkyl,
  mono- and di-lower alkyl amino alkyl
  carbamoyl alkyl,
  mono- and di-carbamoyl alkyl,
  carboxy alkyl,
  alkoxy carbonyl alkyl,
  aralkoxy carbonyl alkyl,
  acyl,
  acylalkyl,
  alkylsulfonyl or
  aralkyl sulfonyl;
R″ and R‴ together may form a 5 to 7 atom ring which may include 0 to 2 hetero atoms of N, O or S;
$R_1$ is hydrogen or lower alkyl provided at least one of R, R′, R″, and R‴ is other than hydrogen; and the pharmaceutically-acceptable salts thereof.

8. The method of claim 7 wherein the amidinourea is 1-(2′6′-dimethylphenyl)-3-methylamidinourea.

9. The method of claim 7 wherein the amidinourea is 1-(2′6′-dimethylphenyl)-3-methylamidinourea hydrochloride.

10. A method for the treatment of primary dysmenorrhea which comprises administering to a menstruating female an effective amount therefor of a compound of the formula:

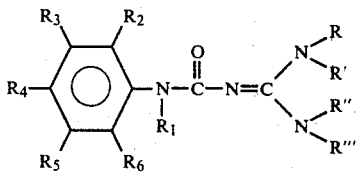

wherein
$R_2$, $R_3$, $R_4$, $R_5$ and $R_6$ are
  hydrogen,
  halo,
  lower alkyl,
  halo lower alkyl,
  nitro,
  hydroxy or,
  lower alkoxy; and,
R′ and $R_1$ are hydrogen or lower alkyl; and
R″ and R‴ are
  hydrogen,
  alkyl or
  alkoxy; provided R, R′, R″ and R‴ are not all hydrogen at the same time
and the non-toxic pharmaceutically-acceptable salts thereof.

11. A method for the treatment of primary dysmenorrhea which comprises administering to a menstruating female an effective amount therefor of a compound of the formula:

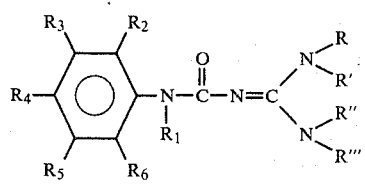

wherein
$R_2$ is hydrogen or lower alkyl,
$R_3$ and $R_5$ are
  hydrogen,
  hydroxy or
  lower alkoxy;
$R_4$ is
  hydrogen,
  lower alkyl,
  hydroxy,
  lower alkoxy or
  halo,
$R_6$ is
  hydrogen,
  lower alkyl,
  nitro,
  alkoxy or
  halo;
R and $R_1$ are hydrogen or alkyl; provided R, R′, R″ and R‴ are not all hydrogen at the same time; and the non-toxic pharmaceutically acceptable salts thereof.

12. A method for the treatment of primary dysmenorrhea which comprises administering to a menstruating female an effective amount therefor of a compound of the formula:

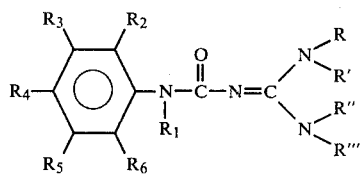

wherein:
$R_2$ is
  hydrogen,
  methyl,
  ethyl,
  chloro or
  bromo;
$R_3$ is
  hydrogen,
  hydroxy, or,
  methoxy;
$R_4$ is
  hydrogen,
  methyl,
  ethyl,
  hyroxy,
  methoxy,
  chloro or
  bromo;
$R_5$ is hydrogen,
hydroxy or
methoxy;
$R_6$ is
 hydrogen,
 methyl,
 ethyl,
 nitro,
 methoxy,
 ethoxy,
 chloro,
 bromo or
 fluoro;
R and $R_1$ are
 hydrogen,
 methyl or
 ethyl; and
R' and R'' are
 hydrogen,
 methyl,
 ethyl,
 propyl,
 i-propyl,
 butyl,
 i-butyl,
 sec-butyl,
 t-butyl,
 methoxy,
 ethoxy,
 propoxy,
 butoxy,
 isopropoxy,
 isobutoxy,
 t-butoxy,
 pentyl,
 hexyl or
 heptyl; provided R, R', R'' and R''' are not all hydrogen at the same time;

and the non-toxic pharmaceutically acceptable salts thereof.

13. The method according to claim 12 wherein $R_2$ and $R_6$ are each separately hydrogen, methyl or ethyl, and $R_3$ and $R_5$ are each hydrogen.

14. The method according to claim 13 wherein $R_4$ is hydrogen, methyl or ethyl.

15. The method according to claim 12 wherein $R_1$ is hydrogen and R, R', R'' and R''' are each separately hydrogen, methyl, ethyl, propyl, isopropyl, methoxy, ethoxy or propoxy.

16. The method according to claim 15 wherein $R_3$ and $R_5$ are each hydrogen, and $R_2$, $R_4$ and $R_6$ are each separately hydrogen, methyl, ethyl, chloro or bromo.

17. The method according to claim 16 wherein $R_4$ is hydrogen.

18. The method according to claim 17 wherein $R_2$ and $R_6$ are each separately methyl or ethyl.

* * * * *